United States Patent
Lee et al.

(10) Patent No.: US 11,091,449 B2
(45) Date of Patent: Aug. 17, 2021

(54) GADOBUTROL INTERMEDIATE AND GADOBUTROL PRODUCTION METHOD USING SAME

(71) Applicant: ENZYCHEM LIFESCIENCES CORPORATION, Daejeon (KR)

(72) Inventors: Jae Young Lee, Yongin-si (KR); Jong Soo Lee, Wonju-si (KR); Byung Kyu Kang, Jecheon-si (KR); Sang Oh Lee, Daejeon (KR); Byouong Woo Lee, Jecheon-si (KR); Dae Myoung Yun, Wonju-si (KR); Jae Hun Bang, Daegu (KR); Choi Kyung Seok, Seoul (KR)

(73) Assignee: ENZYCHEM LIFESCIENCES CORPORATION, Daejeon (KR)

( * ) Notice: Subject to any disclaimer, the term of this patent is extended or adjusted under 35 U.S.C. 154(b) by 0 days.

(21) Appl. No.: 16/642,108

(22) PCT Filed: Aug. 29, 2018

(86) PCT No.: PCT/KR2018/009956
§ 371 (c)(1),
(2) Date: Feb. 26, 2020

(87) PCT Pub. No.: WO2019/045436
PCT Pub. Date: Mar. 7, 2019

(65) Prior Publication Data
US 2020/0181098 A1    Jun. 11, 2020

(30) Foreign Application Priority Data

Aug. 29, 2017  (KR) .................. 10-2017-0109677

(51) Int. Cl.
| A61K 49/10 | (2006.01) |
| C07D 257/02 | (2006.01) |
| C07F 5/00 | (2006.01) |

(52) U.S. Cl.
CPC .......... *C07D 257/02* (2013.01); *A61K 49/108* (2013.01); *C07B 2200/13* (2013.01)

(58) Field of Classification Search
CPC ............................ A61K 49/108; C07D 257/02
See application file for complete search history.

(56) References Cited

U.S. PATENT DOCUMENTS

| 5,962,679 | A | 10/1999 | Ripa et al. |
| 5,977,353 | A | 11/1999 | Argese et al. |
| 5,980,864 | A | 11/1999 | Platzek et al. |
| 5,994,536 | A * | 11/1999 | Petrov ................. C07D 257/02 540/474 |
| 6,020,485 | A | 2/2000 | Argese et al. |
| 6,028,194 | A | 2/2000 | Argese et al. |
| 6,042,810 | A * | 3/2000 | Ripa .................. C07D 257/02 424/9.363 |
| 6,048,980 | A | 4/2000 | Argese et al. |
| 6,054,581 | A | 4/2000 | Ripa et al. |
| 6,162,912 | A | 12/2000 | Argese et al. |
| 6,166,201 | A | 12/2000 | Ripa et al. |
| 10,065,933 | B2 | 9/2018 | Lim et al. |
| 10,072,027 | B2 | 9/2018 | Platzek et al. |
| 10,435,417 | B2 | 10/2019 | Platzek et al. |
| 2013/0116429 | A1 | 5/2013 | Platzek |
| 2014/0107325 | A1 * | 4/2014 | Platzek ............... C07D 257/02 534/16 |
| 2017/0342038 | A1 | 11/2017 | Lim et al. |
| 2018/0105537 | A1 | 4/2018 | Platzek et al. |

FOREIGN PATENT DOCUMENTS

| KR | 10-2014-0035911 | 3/2014 |
| KR | 10-2016-0056648 | 5/2016 |
| KR | 10-2016-0079460 | 7/2016 |
| WO | 98/55467 | 12/1998 |
| WO | 98/056776 | 12/1998 |
| WO | 99/05145 | 2/1999 |
| WO | 2011/151347 | 12/2011 |
| WO | 2012/143355 | 10/2012 |

OTHER PUBLICATIONS

J. Platzek et al., Synthesis and Structure of a New Macrocyclic Polyhydroxylated Gadolinium Chelate Used as a Contrast Agent for Magnetic Resonacne Imaging, Inorg. Chem, 36, 6086-6093. (Year: 1997).*

Platzek, J. et al., "Synthesis and Structure of a New Macrocyclic Polyhydroxylated Gadolinium Chelate Used as a Contrast Agent for Magnetic Resonance Imaging", Inorganic Chemistry, 1997, vol. 36, pp. 6086-6093.

* cited by examiner

*Primary Examiner* — Michael G. Hartley
*Assistant Examiner* — Jagadishwar R Samala
(74) *Attorney, Agent, or Firm* — Lex IP Meister, PLLC

(57) ABSTRACT

Disclosed are: an intermediate capable of high-purity synthesis of gadobutrol which can be used as an MRI contrast agent; and a gadobutrol production method using same. The gadobutrol intermediate is represented by Chemical Formula 2 in the specification.

2 Claims, No Drawings

GADOBUTROL INTERMEDIATE AND GADOBUTROL PRODUCTION METHOD USING SAME

TECHNICAL FIELD

The present disclosure relates to a gadobutrol intermediate and a gadobutrol production method using the same, and more particularly, to an intermediate capable of synthesizing gadobutrol, which is used as a magnetic resonance imaging (MRI) contrast agent, with high purity, and a gadobutrol production method using the same.

BACKGROUND ART

Gadobutrol, which is a kind of magnetic resonance imaging (MRI) contrast agents, having asymmetric macrocycles and containing gadolinium, is commercially available under the trade names Gadovist or Gadavist. A contrast action of the gadobutrol is based on a nonionic complex consisting of gadolinium cation and 2,2,2-((10-1,3,4-trihydroxybutan-2-yl)-1,4,7,10-tetraazacyclododecane-1,4,7-triyl)triacetic acid (hereafter, butrol) which is a macrocyclic ligand. The macrocycles and nonionic structure allow gadobutrol to have relatively excellent physical properties and high safety in the body as compared to the conventional commercially available ionic gadolinium-containing MRI contrast agents such as gadopentetate monomeglumine, gadopentetate dimeglumine, and the like.

Gadobutrol, which is non-ionic, has lower osmotic pressure and viscosity than those of ionic gadolinium-containing MRI contrast agents, which is capable of reducing side effects such as local response, and the like, at the time of extravasation of the contrast agent. The macrocyclic ligand structure based on the butrol of gadobutrol is in the form of a cage, and is strongly bound to the gadolinium cations, and thus the gadolinium cations are not easily released as compared to gadopentetate monomeglumine and gadopentetate dimeglumine, and the like, having a linear ligand structure. Thus, safety against nephrogenic systemic fibrosis (NSF) due to the toxicity of free gadolinium cations in the body when injected is also high.

As shown in the following Chemical Formula 5, there are currently two ways to synthesize butrol, which is a core precursor of gadobutrol, by first introducing a trihydroxy butane group at a position No. 10 of the starting material cyclen, and then introducing a triacetic acid group at position Nos. 1, 4, and 7 thereof, and in contrast, by first introducing the triacetic acid group at position Nos. 1, 4, and 7, and then introducing the trihydroxy butane group at position No. 10:

The former method employs a reagent such as DMF Acetal, or the like, to selectively react only one amine reaction group of cyclen, thereby introducing the trihydroxy group (WO211151347A1, US005980864A), or employs a lithium-halogen complex of cyclen to selectively introduce the trihydroxy group (WO98/55467, WO212/143355). The latter method also employs the reagent such as DMF Acetal, or the like, to selectively protect only one amine reaction group of cyclen, and then repeats further reaction and a process of deprotection group (EP2001/058988, US005962679, WO98/056776, and the like) or employs a derivative of cyclen in which the amine reaction group of cyclen is protected in a bicyclic form (WO99/05145).

However, these conventional methods have disadvantages, for example, materials such as DMF Acetal, which are known to cause fetal malformations and are relatively expensive, are used (EP2001/058988, US005962679, WO98/056776, WO211151347A1, US005980864A), or a precursor, which is difficult to be synthesized as a derivative of cyclen rather than cyclen, is used (WO99/05145), or all reactions should proceed in situ and there is no purification of intermediates, and thus it is relatively difficult to perform purification and process control (WO2012/143355, WO2011/151347A1). In addition, the MRI contrast agents used in the form of injections as well as gadobutrol have common difficulties due to their characteristics in that solubility in organic solvents is low, and hydrophilicity is high, and thus it is difficult to remove by-products of inorganic salts generated during the synthesis of the product by simple washing or crystallization. Therefore, there is a need to improve the process for producing gadobutrol with high purity.

TECHNICAL PROBLEM

An object of the present disclosure is to provide a gadobutrol intermediate capable of producing gadobutrol with high purity by reducing a salt content, and a gadobutrol production method using the same.

Another object of the present disclosure is to provide a gadobutrol intermediate capable of producing gadobutrol economically with easy process control, and a gadobutrol production method using the same.

TECHNICAL SOLUTION

In one general aspect, there is provided a gadobutrol intermediate represented by the following Chemical Formula 2:

[Chemical Formula 5]

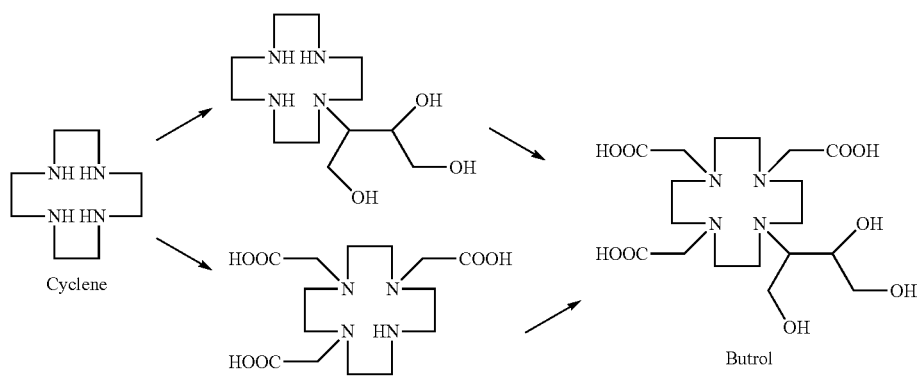

[Chemical Formula 2]

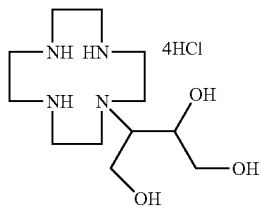

In another general aspect, there is provided a gadobutrol intermediate production method including: reacting 1,4,7,10-tetraazacyclododecane with a lithium-halogen salt to produce a cyclen-lithium halogen complex, followed by reaction with 4,4-dimethyl-3,5,8-trioxabicyclo[5,1,0]octane to obtain N-(6-hydroxy-2,2-dimethyl-1,3-dioxyphen-5-yl)-1,4,7,10-tetraazacyclododecane-lithium halogen complex represented by the following Chemical Formula 1; and reacting the lithium halogen complex represented by Chemical Formula 1 with hydrochloric acid to obtain the compound represented by Chemical Formula 2:

[Chemical Formula 1]

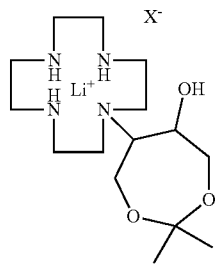

In still another general aspect, there is provided a gadobutrol production method including: alkylating the gadobutrol intermediate represented by Chemical Formula 2 with chloroacetic acid to obtain a butrol represented by the following Chemical Formula 3; and reacting the butrol represented by Chemical Formula 3 with gadolinium oxide:

[Chemical Formula 3]

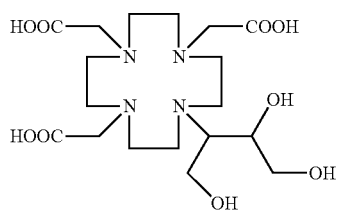

ADVANTAGEOUS EFFECTS

According to the gadobutrol intermediate and the gadobutrol production method using the same described in the present disclosure, it is possible to not only produce the gadobutrol with high purity, but also to produce the gadobutrol economically with easy process control.

BEST MODE FOR CARRYING OUT THE INVENTION

Hereinafter, the following disclosure is described in more detail.

In order to produce a gadobutrol intermediate according to the present disclosure, first, a cyclen-lithium halogen complex is produced by reacting 1,4,7,10-tetraazacyclododecane (hereinafter referred to as "cyclen") as a starting material and a lithium-halogen salt. The reaction may be performed in an alcohol solvent such as tert-butanol, ethanol, isopropyl alcohol, or the like, and a reaction temperature is generally 85 to 95° C. Examples of the lithium-halogen salt may include lithium chloride, lithium bromide, and the like. An amount of the lithium-halogen salt used is 1.0 to 1.5 equivalents, preferably 1.2 to 1.4 equivalents based on 1 equivalent of cyclen. Here, if the amount of the lithium-halogen salt used is excessively small, there is a problem in view of yield since the reaction selectivity is poor, and if the amount thereof is excessively large, there is a problem of reduction in yield due to formation of a flexible material. When the thus-obtained cyclen-lithium halogen complex and 4,4-dimethyl-3,5,8-trioxabicyclo[5,1,0]octane are reacted, N-(6-hydroxy-2,2-dimethyl-1,3-dioxyphen-5-yl)-1,4,7,10-tetraazacyclododecane-lithium halogen complex represented by the following Chemical Formula 1 is obtained. Here, X is halogen.

[Chemical Formula 1]

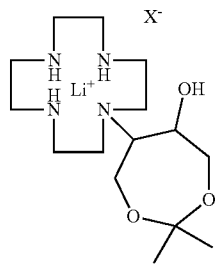

In the above reaction, an amount of 4,4-dimethyl-3,5,8-trioxabicyclo[5,1,0]octane used is 1.0 to 1.5 equivalents, preferably 1.2 to 1.4 equivalents based on the cyclen-lithium halogen complex. Here, if the amount of the 4,4-dimethyl-3,5,8-trioxabicyclo[5,1,0]octane is excessively small, there is a problem of reduction in yield due to unreacted materials, and if the amount thereof is excessively large, there is a problem of reduction in purity and yield due to pyrolysis products.

Next, the lithium halogen complex represented by Chemical Formula 1 is reacted with hydrochloric acid to obtain a gadobutrol intermediate (3-(1,4,7,10-tetraazacyclododecane-1-yl)butane)-1,2,4-triol tetrahydrochloride) represented by the following Chemical Formula 2:

[Chemical Formula 2]

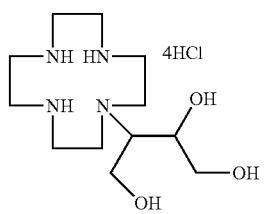

In the above reaction, an amount of hydrochloric acid used is 4.0 to 5.0 equivalents, preferably 4.0 to 4.2 equivalents based on the lithium halogen complex represented by Chemical Formula 1. Here, if the amount of the hydrochloric acid is excessively small, there is a problem that the yield is reduced, and if the amount thereof is excessively large, there is a problem that the impurities increase due to strong acid. The reaction for synthesizing the hydrochloride may be performed by adding hydrochloric acid to the reaction solution to which the compound of Chemical Formula 1 is synthesized, without purifying the reaction solution in which the compound of Chemical Formula 1 is obtained or separately separating the compound of Chemical Formula 1. When the hydrochloride represented by Chemical Formula 2 is separated and purified from the reactant by filtration, or the like, it is possible to obtain the gadobutrol intermediate represented by Chemical Formula 2 in a crystalline form with high purity.

Next, a gadobutrol production method using the gadobutrol intermediate represented by Chemical Formula 2 is described.

First, the gadobutrol intermediate represented by Chemical Formula 2 is alkylated with chloroacetic acid to obtain a compound represented by the following Chemical Formula 3 (butrol, 2,2,2-((10-1,3,4-trihydroxybutan-2-yl)-1,4,7,10-tetraazacyclododecane-1,4,7-triyl)triacetic acid):

[Chemical Formula 3]

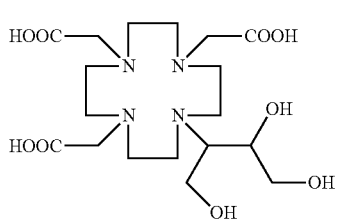

The reaction may be performed in an alkaline water solvent. For example, the solvent for the reaction may be prepared by adding dropwise sodium hydroxide (NaOH) to water to form an alkaline medium having the pH of 9 to 10. The reaction may generally be performed at a temperature of 75 to 85° C. In the above reaction, an amount of chloroacetic acid used is 3.0 to 4.5 equivalents, preferably 3.4 to 4.0 equivalents based on the gadobutrol intermediate represented by Chemical Formula 2. Here, if the amount of the chloroacetic acid is excessively small, there is a problem of reduction in yield and purity due to unreacted products, and if the amount thereof is excessively large, there is a problem in removing unreacted products and degraded products.

The reactant is concentrated under acidic conditions, filtered, and specifically, purified using nanofiltration systems. The nanofiltration system, which is a spiral type reverse osmosis device with an organic membrane, may filter or concentrate substances having a molar mass of 200 to 300 daltons or more, and may separate and purify salts and other water-soluble organic-inorganic materials having low molecular weights through the organic membrane to recover only desired materials. The reactant may be filtered through the nanofiltration system to obtain the compound represented by Chemical Formula 3 from which impurities are removed.

Next, the butrol represented by Chemical Formula 3 is reacted with gadolinium oxide to obtain gadobutrol represented by the following Chemical Formula 4 (2,2,2-((10-1,3,4-trihydroxybutan-2-yl)-1,4,7,10-tetraazacyclododecane-1,4,7-triyl)triacetic acid, gadolinium complex):

[Chemical Formula 4]

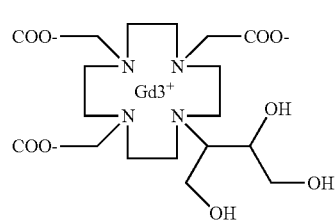

In the above reaction, an amount of gadolinium oxide used is 0.3 to 1.0 equivalents, preferably 0.4 to 0.6 equivalents based on 1 equivalent of the butrol represented by Chemical Formula 3. Here, if the amount of the gadolinium oxide is excessively small, there is a problem of reduction in yield, and there is a problem in removing the unreacted butrol, and if the amount thereof is excessively large, there is a problem of poor filterability due to the remaining gadolinium oxide. A reaction temperature of the reaction is generally 80 to 90° C.

When the reactant is purified and separated by a method such as an ion exchange resin, or the like, gadobutrol with a purity of 99.7% or more may be obtained. As the ion exchange resin, it is possible to employ an ion exchange resin in a cascaded manner with a cation exchange resin column and an anion exchange resin column. The crude gadobutrol compound as purified above may be dissolved in purified water and crystallized and isolated with alcohol. More specifically, the crude gadobutrol compound may be recrystallized by twice repetition in water-methanol conditions, and isolated in water-ethanol conditions. As a crystallization solvent, alcohol solvents such as methanol, ethanol, tert-butanol, isopropanol, and the like, may be used, and a mixed solvent of water and alcohol consisting of 5.0 to 15% by weight of water and the remaining alcohol may also be used. The crystals obtained above may generally be dried at 40 to 45° C. to obtain gadobutrol with high purity.

DETAILED DESCRIPTION OF EMBODIMENTS

Hereinafter, the present disclosure is described in more detail with reference to the following Examples, but the present disclosure is not limited by the Examples.

[Example 1] Production of Gadobutrol Intermediate Represented by Chemical Formula 2

1,4,7,10-tetraazacyclododecane (59.7 Kg, 1 e.q.), lithium chloride (17.64 Kg, 1.14 e.q.), 4,4-dimethyl-3,5,8-trioxabicyclo[5.1.0]octane (50.0 Kg, 1 e.q.) and isopropyl alcohol (131.1 kg, 2.2 vol.) were added to a reactor and reacted by raising a temperature to 85 to 95° C. After the reaction, 495.8 Kg of methyl tert-butyl ether was added thereto, and the mixture was stirred at 20 to 25° C. for 1 hour, filtered, and washed with 47.5 kg of methyl tert-butyl ether. The filtrate was concentrated under reduced pressure, 176.8 Kg of methanol was added thereto, 163.4 Kg of hydrochloric acid was added thereto, and the mixture was stirred under reflux for 3 hours, and then concentrated under reduced pressure.

The obtained product was concentrated under reduced pressure by adding 266.3 kg of methanol (MeOH) thereto, and then was concentrated under reduced pressure by adding 266.3 kg of methanol thereto. 319.5 kg of methanol was added thereto, and the mixture was stirred under reflux for 3 hours, cooled to 0 to 5° C., stirred for 1 hour, then washed with 53.3 kg of methanol for filtration, and dried to obtain 107.5 Kg of 3-(1,4,7,10-tetraazacyclododecane-1-yl)butane-1,2,4-triol tetrahydrochloride (yield 73.4%, purity 98% (HPLC)).

[Example 2] Production of Gadobutrol Represented by Chemical Formula 4

Step A: Production of Butrol 3-(1,4,7,10-tetraazacyclododecane-1-yl)butane-1,2,4-triol tetrahydrochloride (107.5 Kg, 1 e.q.), 2-chloroacetic acid (91.33 Kg, 4.3 e.q.), and purified water (429.6 Kg, 4 vol.) were added to the reactor. Then, the mixture was heated and stirred to 75 to 85° C. while maintaining pH 9 to 10 by adding dropwise 40% NaOH, thereby terminating the reaction. 133.9 Kg of hydrochloric acid was added to the mixture, and the mixture was concentrated under reduced pressure. 169.7 Kg of methanol was added to filter the salt, followed by nano-filtering to obtain 2,2,2-(10-1,3,4-trihydroxybutan-2-yl)-1,4,7,10-tetraazacyclododecane-1,4,7-triyl)triacetic acid to proceed with the next reaction.

Step B: Production of Gadobutrol

After the nano-filtering, the filtrate was added to the reactor, and gadolinium oxide (46.1 Kg, 1.5 e.q.) was added thereto. The temperature was raised to 80 to 90° C., and then the mixture was heated and stirred to terminate the reaction. Then, the obtained product was purified by sequentially passing anionic and cationic resins therethrough, and then concentrated under reduced pressure. 90 kg of purified water was added thereto, the temperature was raised to 60 to 70° C., 853.2 Kg of methanol was added thereto, and the mixture was cooled to 0 to 5° C., filtered, washed with 71.1 Kg of methanol, and crystallized. 90 kg of purified water was added to dissolve the crystallized gadolinium complex, the temperature was raised to 60 to 70° C., then 853.2 Kg of methanol was added thereto, and the mixture was cooled to 0 to 5° C., filtered, washed with 71.1 Kg of methanol, and purified. The obtained product was dissolved by adding 90 kg of purified water, filtered, and the temperature was raised to 75 to 85° C., then 2559.6 kg of anhydrous ethanol was added thereto. The obtained product was cooled to 0 to 5° C., stirred for 1 hour, filtered, washed with 169.7 kg of anhydrous ethanol, and dried to obtain 93.8 Kg (yield 60.9%) of gadolinium complex of 2,2,2-(10-1,3,4-trihydroxybutan-2-yl)-1,4,7,10-tetraazacyclododecane-1,4,7-triyl)triacetic acid, with purity of 99.8% (HPLC).

The invention claimed is:

1. A gadobutrol production method comprising:
reacting 1,4,7,10-tetraazacyclododecane with a lithium-halogen salt to produce a cyclen-lithium halogen complex, followed by reaction with 4,4-dimethyl-3,5,8-trioxabicyclo[5,1,0]octane to obtain N-(6-hydroxy-2,2-dimethyl-1,3-dioxyphen-5-yl)-1,4,7,10-tetraazacyclododecane-lithium halogen complex represented by the following Chemical Formula 1 (wherein X is a halogen);

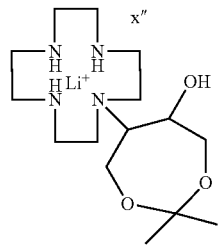

[Chemical Formula 1]

reacting the lithium halogen complex represented by Chemical Formula 1 with hydrochloric acid to obtain a gadobutrol intermediate represented by the following Chemical Formula 2;

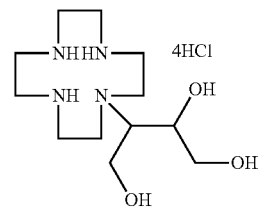

[Chemical Formula 2]

filtering a reactant of the lithium halogen complex represented by Chemical Formula 1 and the hydrochloric acid to obtain the gadobutrol intermediate represented by Chemical Formula 2 in a crystalline form;
alkylating the gadobutrol intermediate represented by the Chemical Formula 2 with chloroacetic acid to obtain a butrol represented by the following Chemical Formula 3; and
reacting the butrol represented by Chemical Formula 3 with gadolinium oxide,

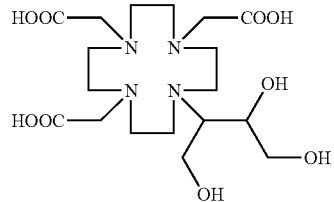

[Chemical Formula 3]

wherein an amount of the hydrochloric acid is 4.0 to 4.2 equivalents based on the lithium halogen complex represented by Chemical Formula 1.

2. The gadobutrol production method of claim 1, further comprising:
purifying a reactant of the gadobutrol intermediate and chloroacetic acid by filtering a salt and a water-soluble low-molecular material corresponding to 100 to 300 daltons using a nanofiltration system.

* * * * *